(12) United States Patent
Walinsky et al.

(10) Patent No.: US 6,570,018 B2
(45) Date of Patent: May 27, 2003

(54) PROCESS FOR THE PREPARATION OF THE MESYLATE SALT TRIHYDRATE OF 1-(4-HYDROXYPHENYL)-2-(4-HYDROXY-4-PHENYLPIPERIDIN-1-YL)-1-PROPANOL AND INTERMEDIATES USEFUL THEREFOR

(75) Inventors: Stanley Walter Walinsky, Mystic, CT (US); Terry Gene Sinay, Jr., Preston, CT (US); Joseph Philip Rainville, Uncasville, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/840,668

(22) Filed: Apr. 23, 2001

(65) Prior Publication Data

US 2002/0016466 A1 Feb. 7, 2002

Related U.S. Application Data

(60) Provisional application No. 60/200,417, filed on Apr. 28, 2000.

(51) Int. Cl.[7] .................. C07D 211/52; C07D 211/48

(52) U.S. Cl. ............................. 546/217; 514/327

(58) Field of Search ..................... 514/327; 546/217

(56) References Cited

U.S. PATENT DOCUMENTS 5,716,961 A  * 2/1998 Sands .................. 514/277
6,008,233 A    12/1999 Andino et al. .......... 514/327

OTHER PUBLICATIONS

Hideji Takamatsu, "Studies on Optically Active Phenylpropanolamine Derivatives. I. Preparation of Optically Active α–Aminopropiophenones by Asymmetric Transformation," *J. Pharm. Japan*, 76 (11), pp. 1219–1222 (1956).

* cited by examiner

*Primary Examiner*—Ceila Chang
(74) *Attorney, Agent, or Firm*—Peter C. Richardson; Paul H. Ginsburg; E. Victor Donahue

(57) ABSTRACT

The present invention is directed to a novel process for the preparation of the mesylate trihydrate of the compound of formula (I), (1S,2S)-1-(4-hydroxyphenyl)-2-(4-hydroxy-4-phenylpiperidin-1-yl)-1-propanol:

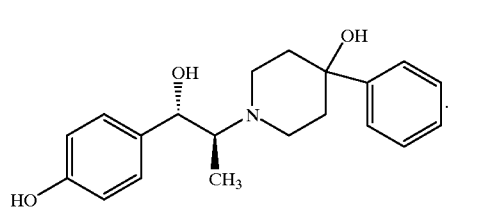

(I)

The present invention is further directed to a process for the preparation of a (2S)-(+)-compound of formula (II):

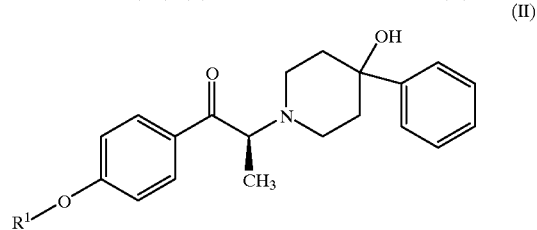

(II)

wherein $R^1$ is a protecting group. In addition, the present invention relates to intermediates useful in said processes.

3 Claims, No Drawings

PROCESS FOR THE PREPARATION OF THE MESYLATE SALT TRIHYDRATE OF 1-(4-HYDROXYPHENYL)-2-(4-HYDROXY-4-PHENYLPIPERIDIN-1-YL)-1-PROPANOL AND INTERMEDIATES USEFUL THEREFOR

This application claims the benefit of U.S. provisional patent application Ser. No. 60/200,417, filed Apr. 28, 2000.

The present invention is directed to a process for the preparation of the mesylate trihydrate of the compound of formula (I), (1S,2S)-1-(4-hydroxyphenyl)-2-(4-hydroxy-4-phenylpiperidin-1-yl)-1-propanol:

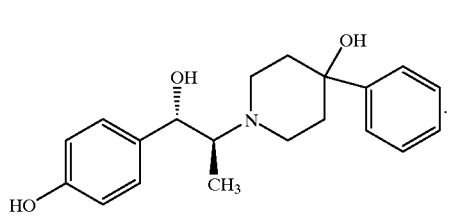

(I)

The present invention is further directed to a process for the preparation of the (2S)-(+)-enantiomer of formula (II):

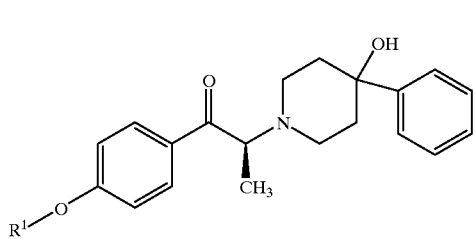

(II)

wherein $R^1$ is a protecting group selected from the group consisting of benzyl, $(C_1-C_6)$alkylbenzyl, $(C_1-C_6)$alkoxylbenzyl, tri$(C_1-C_6)$alkylsilyl, acyl (e.g., acetyl) and aroyl (e.g., benzoate). In addition, the present invention relates to intermediates useful in said processes.

The compound of formula (I), (1S,2S)-1-(4-hydroxyphenyl)-2-(4-hydroxy-4-phenylpiperidin-1-yl)-1-propanol, exhibits potent activity as an NMDA (N-methyl-D-aspartic acid) receptor antagonist and is useful in the treatment of epilepsy, anxiety, cerebral ischemia, muscular spasms, multi-infarct dementia, traumatic brain injury, pain, AIDS-related dementia, hypoglycemia, migraine, amyotrophic lateral sclerosis, drug and alcohol addiction, drug and alcohol withdrawal symptoms, psychotic conditions, urinary incontinence and degenerative CNS (central nervous system) disorders such as stroke, Alzheimer's disease, Parkinson's disease and Huntington's disease.

The mesylate trihydrate form of (1S,2S)-1-(4-hydroxyphenyl)-2-(4-hydroxy-4-phenylpiperidin-1-yl)-1-propanol is superior to the anhydrous mesylate as an active therapeutic agent because of its properties. The mesylate trihydrate has a more stable crystalline form than the anhydrous mesylate salt, and hence, a substantially longer shelf life. The trihydrate is also less subject to breakdown in crystal structure due to the inclusion of water in the crystal. U.S. Pat. No. 6,008,233 describes the mesylate salt trihydrate, the anhydrous mesylate salt and free base of (1S,2S)-1-(4-hydroxyphenyl)-2-(4-hydroxy-4-phenylpiperidin-1-yl)-1-propanol, and methods for their preparation.

Further, the free base of formula (I), its anhydrous mesylate, and methods of preparing them are also referred to, generically, in U.S. Pat. No. 5,185,343, which issued on Feb. 9, 1993. Their use in treating certain of the above disorders are referred to, specifically, in U.S. Pat. No. 5,272,160, which issued on Dec. 21, 1993; and International Patent Application PCT/IB 95/00380, which designates the United States, filed on May 18, 1995 and published as WO 96/06081. Their use in combination with a compound capable of enhancing and thus restoring the balance of excitatory feedback from the ventral lateral nucleus of the thalamus into the cortex to treat Parkinson's disease is referred to in International Patent Application PCT/IB 95/00398, which designates the United States, filed on May 26, 1995 and published as WO96/37226. The foregoing U.S. patents and patent applications are incorporated herein by reference in their entireties.

Previous methods for the preparation of the (1S,2S)-1-(4-hydroxyphenyl)-2-(4-hydroxy-4-phenylpiperidin-1-yl)-1-propanol proceeded via racemic synthetic pathways with resolution of the active optical isomers in the steps prior to therapeutic salt formation. One of the problems associated with resolution of compounds relatively late in a synthetic scheme is the waste and reduced efficiency involved in disposing of significant amounts of inactive or less active enantiomers and diastereomers. To maximize the efficacy of the synthesis, it is desirable to have a synthesis which introduces centers of optical activity into the target molecule precursors early in the synthesis. Accordingly, a method for transforming a racemic starting material into an optically active building block for the directed chiral synthetic pathway to a compound of formula (I) would be a significant advantage.

Although methods for the asymmetric transformation of racemic materials to chiral ones have been reported, the ability to obtain successfully optically active products has often been strictly limited to the specific circumstances and compounds involved. The preparation of optically active α-aminopropiophenones has been achieved by asymmetric transformation. Takamatsu, *J. Pharm. Soc. Japan*, 76(11), 1219–1222 (1956). In addition, the transformation of racemic 3-(RS)-amino-1,3-dihydro-1-methyl-5-phenyl-2H-1,4-benzodiazepin-2-one to its nearly optically pure (S)-enantiomer by crystallization induced asymmetric transformation has been reported. Reider et al., *J. Org. Chem.*, 52, 955–957 (1987).

SUMMARY OF THE INVENTION

The present invention relates to a process for the preparation of the methanesulfonate trihydrate salt of (1S,2S)-1-(4-hydroxyphenyl)-2-(4-hydroxy-4-phenylpiperidin-1-yl)-1-propanol:

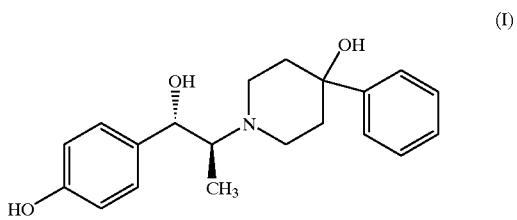

(I)

comprising the steps of (i) reducing the carbonyl group of a compound of formula (II)

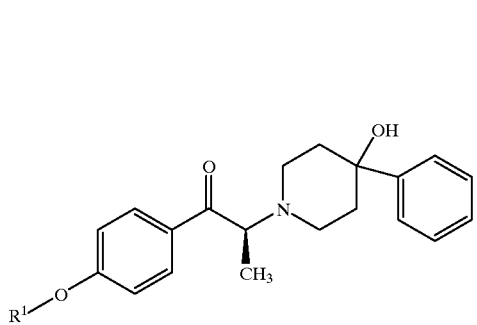

wherein $R^1$ is a protecting group, selected from the group consisting of benzyl, $(C_1-C_6)$alkylbenzyl, $(C_1-C_6)$alkoxylbenzyl, tri$(C_1-C_6)$alkylsilyl, acyl (e.g., acetyl) and aroyl (e.g., benzoate), via reaction with a alkali metal borohydride; and (ii) cleaving off the protecting group $R^1$ of a compound of formula (III)

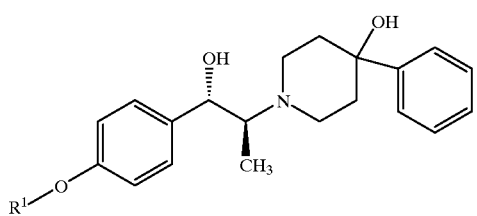

in the presence of methanesulfonic acid.

A preferred embodiment of the invention is where the protecting group $R^1$ is benzyl, $(C_1-C_6)$alkylbenzyl or $(C_1-C_6)$alkoxylbenzyl. Another preferred embodiment is wherein the alkali metal borohydride is lithium borohydride or sodium borohydride. A more preferred embodiment of the invention is wherein the $R^1$ group is benzyl and the alkali metal borohydride is lithium borohydride.

Another preferred embodiment is wherein the protecting group $R^1$ is benzyl and the cleavage of the protecting group of step (ii) is hydrogenolysis conducted in the presence of hydrogen gas and 5%–20% palladium on carbon. A more preferred embodiment is wherein the $R^1$ group is benzyl and the hydrogenolysis is conducted in the presence of hydrogen gas and 5% palladium on carbon. A preferred embodiment of the invention is wherein steps (i) and (ii) are conducted in a $(C_1-C_6)$ alkanol solvent, optionally admixed with water. A more preferred embodiment of the invention is wherein the solvent used in steps (i) and (ii) is ethanol admixed with water.

The invention is also directed to a process for the preparation a compound of formula (II):

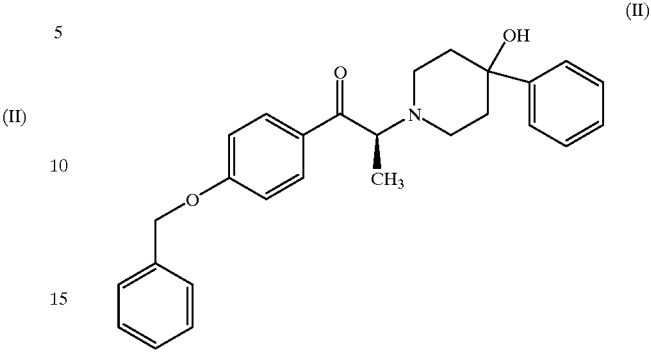

comprising the steps of (i) placing a compound of formula (IV):

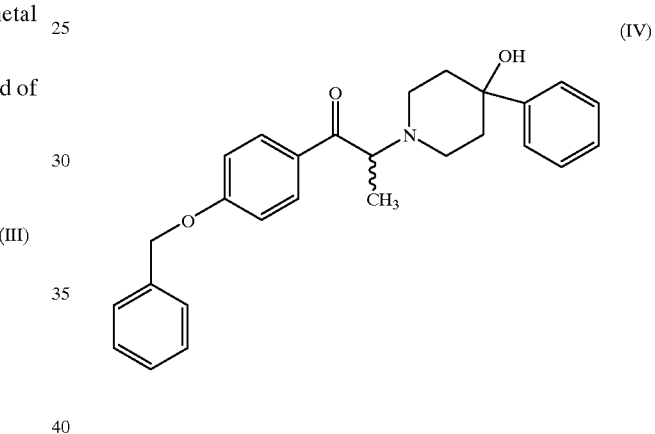

together with a diaroyl D-tartrate;

(ii) treating the D-tartrate salt product of step (i) with a weak base.

A "weak base," as referred to herein, is a basic compound which is not sufficient in basicity to remove readily the α-proton from a compound of formula (IV). A preferred embodiment of the invention is wherein the diaroyl D-tartrate is dibenzoyl D-tartrate or di-p-toluoyl D-tartrate. A preferred embodiment of the invention is wherein the steps of this process are conducted in a lower alkyl ketonic solvent, more preferably acetone. The more preferred embodiment of the invention is wherein the steps of this process are conducted in acetone at a temperature between 25° C. and the reflux temperature, most preferably between 48 and 52° C.

A preferred embodiment of the invention is wherein the weak base is a tri$(C_1-C_6)$alkylamine or an alkali/alkaline-earth metal carbonate, bicarbonate or alkylcarboxylate, e.g., $NaHCO_3$, $Na_2CO_3$, $NaOOCCH_3$, etc. A more preferred embodiment of the invention is wherein the weak base is $NaHCO_3$ in water admixed with an organic solvent, such as ethyl acetate or methylene chloride, more preferably, ethyl acetate.

The present invention is also directed to the (2S)-(+)-enantiomer of formula (II):

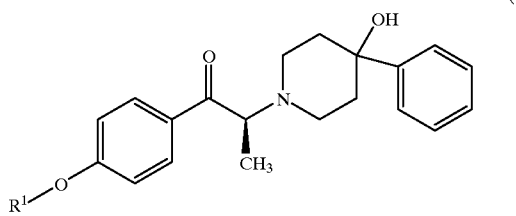
(II)

or a salt thereof, wherein $R^1$ is hydrogen or a protecting group selected from the group consisting of benzyl, $(C_1-C_6)$ alkylbenzyl, $(C_1-C_6)$alkoxylbenzyl, tri$(C_1-C_6)$alkylsilyl, acyl (e.g., acetyl) and aroyl (e.g., benzoate), and the salt is a diaroyl D-tartrate. A preferred embodiment of the invention is wherein $R^1$ is benzyl. Another preferred embodiment of the invention is wherein the diaroyl salt is dibenzoyl D-tartrate salt or di-p-toluoyl D-tartrate.

tions of the mesylate salt trihydrate required the resolution of the racemate of threo-1-(4-hydroxyphenyl)-2-(4-hydroxy-4-phenylpiperidin-1-yl)-1-propanol prior to the formation of the mesylate salt trihydrate. This procedure required the disposal of the less active/inactive (1R,2R) isomer after separation.

The present invention, however, permits the preparation of the mesylate salt trihydrate of a compound of formula (I) by introducing the chiral center at the 2-position of the propanol chain of the final product into the synthetic procedure at an earlier point than previously used in the synthesis of the mesylate trihydrate compound. This early introduction of a chiral center results in a more efficient and higher yielding preparation of the mesylate trihydrate compound without significant formation of enantiomeric and diastereomeric impurities.

The following reaction Scheme illustrates the process of the present invention. The definition of $R^1$ is as above, unless otherwise indicated.

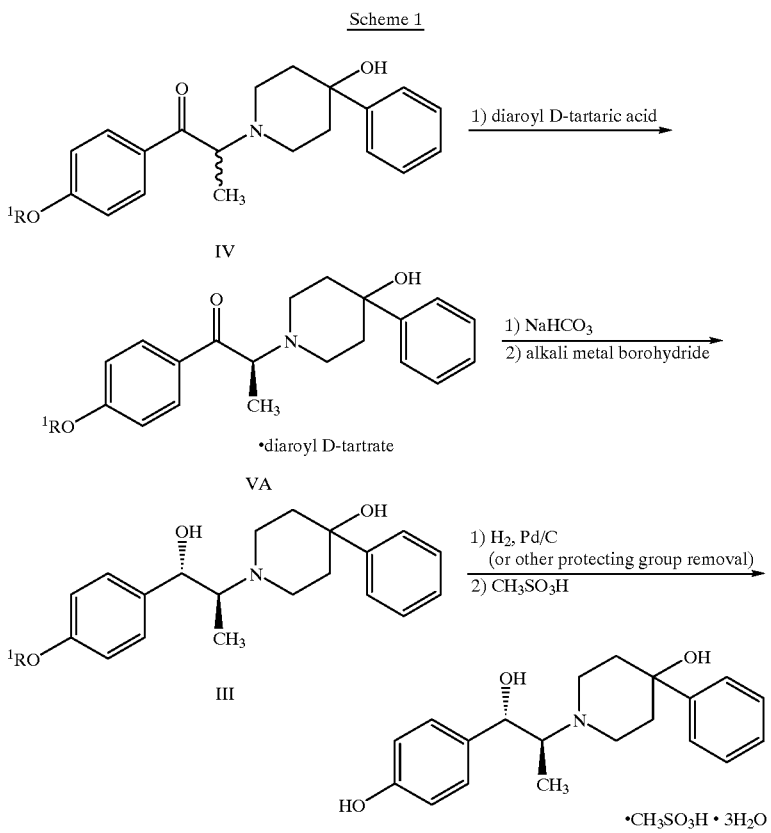

DETAILED DESCRIPTION OF THE INVENTION

The mesylate salt trihydrate of (1S,2S)-1-(4-hydroxyphenyl)-2-(4-hydroxy-4-phenylpiperidin-1-yl)-1-propanol is a white crystalline solid which has a single crystalline form and good solubility in water (25 and 15 mg/mL in pH 3 and 7 aqueous buffered solutions, respectively). The mesylate salt trihydrate is known to form upon allowing the anhydrous mesylate salt to equilibrate in an 81% relative humidity environment. Previous prepara- Referring to Scheme 1, the protected racemic compound of formula (IV) is transformed via crystallization-induced asymmetric transformation into the diaroyl D-tartrate salt of the (2S)-compound of formula (VA), wherein aroyl is benzoyl or p-toluoyl. The acidity of the α-proton allows the chiral center to racemize and set up an equilibrium between the (2S)-compound and its (2R)-antipode, as shown in Scheme 2 below. As seen in Scheme 2, in the presence of diaroyl D-tartaric acid, the crystalline diaroyl D-tartrate salt of the (2S)-(+)-compound of formula (VA) is removed from the steady state due to its relative insolubility, driving the equilibrium with the (2R)-(−)-antipode being eventually transformed to the desired (2S)-(+)-form.

This crystallization induced asymmetric transformation is best achieved in solvents, such as lower alkyl ketonic solvents, e.g., acetone. Optimally, this step is conducted by heating a solution of the compound of formula (IV) and dibenzoyl D-tartaric acid in acetone under an inert atmosphere for approximately 6–7 hours at 48 to 52° C., then cooling to ambient temperature (20 to 25° C.), granulating the resulting slurry, filtering and then drying the obtained salt.

ence of ethyl acetate or methylene chloride, preferably ethyl acetate. The organic layer is then separated, then concentrated, then added to cold hexanes, and then granulated to obtain the free base compound of formula (II).

The compound of formula (II) is then subjected to conditions whereby the carbonyl moiety is reduced without concomitant racemization at the α-position. This can be achieved by exposing the compound of formula (II) to mild reduction conditions, e.g., treatment with an alkali metal borohydride, such as lithium borohydride or sodium borohydride, preferably lithium borohydride, in a solvent Scheme 2

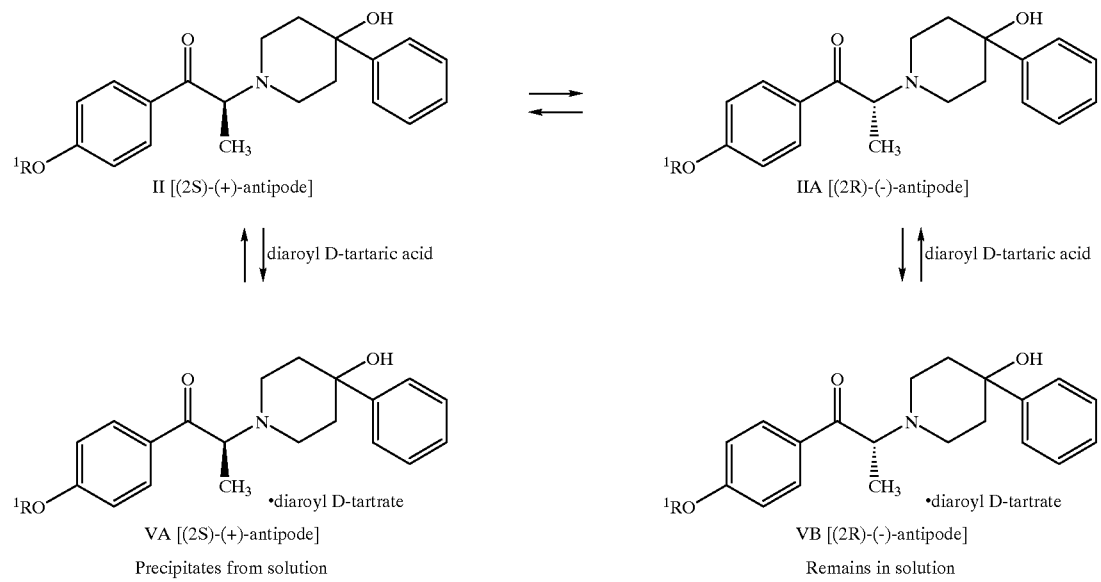

Referring back to Scheme 1, the diaroyl D-tartrate salt of the (2S)-enantiomer of formula (VA) is then treated with a base, preferably aqueous sodium bicarbonate, in the presence of such as, tetrahydrofuran or ethanol, preferably ethanol. A comparison of the different reduction conditions is shown in Table 1.

TABLE 1

Reduction of the Compound of Formula (II) (wherein $R^1$ is benzyl) Under Varied Conditions.

| Reducing Agent (Mol. Equiv) | Solvent | Reaction Time (hrs) | Temp | Reaction Mixture Cmpd (III)* | E | D | Isolated Solids Cmpd (III)* | E | D |
|---|---|---|---|---|---|---|---|---|---|
| $LiBH_4$ (1.6) | (a) | 19.5 | 21–22° C. | 84.1% | — | 15.9% | 79% | 0.1% | 0.5% |
| $LiBH_4$ (1.6) | (a) | 21 | 20–21° C. | 78.9% | 1.7% | 19.4% | — | — | — |
| $NaBH_4$ (1.6) | (a) | 52 | 20–22° C. | 81.7% | 0.4% | 14.6% | 79% | 0.3% | 4.2% |
| $LiBH_4$ (0.8) | (a) | 32 | 20–23° C. | 86% | 1.0% | 13.1% | 84% | 1.5% | 3.0% |
| $NaBH_4$ (0.8) | (a) | 42 | 20–22° C. | 85% | 0.6% | 13.5% | 83% | 0% | 5.3% |
| $KBH_4$ (0.8) | (a) | 48 | 20–22° C. | 88% | Starting Material Unreacted | | | | |
| $Ca(BH_4)_2$ (0.8) | (a) | 48 | 20–22° C. | 90% | Starting Material Unreacted | | | | |
| K Selectride (1.1) | (b) | 1 | 0.5° C. | — | — | — | 46% | 34% | — |

E = (1R,2R)-enantiomer
D = Other diastereomers
(a) ethanol (10 mL/g Cmpd IV)
(b) THF (2.0 mL/g Cmpd IV)
*$R^1$ is benzyl The protecting group $R^1$ of the product compound of formula (III) is then best removed by hydrogenolysis if that protecting group is benzyl, $(C_1-C_6)$alkylbenzyl or $(C_1-C_6)$ alkoxylbenzyl. When the protecting group $R^1$ is tri$(C_1-C_6)$ alkylsilyl, acyl (e.g., acetyl) or aroyl (e.g., benzoate), it may be removed via conventional techniques known to those in the chemical arts, i.e., treatment with fluoride ion for the silyl group removal or hydrolysis techniques for the acyl/ aroyl ester cleavage.

When $R^1$ is benzyl, this protecting group is effectively removed by the use of hydrogen gas with a 5–20% palladium on carbon, in an appropriate solvent, such as tetrahydrofuran, to obtain the free base. However, the hydrogenolysis reaction may be conducted with or without the presence of methanesulfonic acid, depending on whether the desired product is the free base or the mesylate salt. When conducted in the presence of methanesulfonic acid, the hydrogenolysis reaction is conducted in a $(C_1-C_6)$ alkanol, optionally in admixture with water, preferably ethanol in admixture with water, the mesylate salt is formed in situ. When the reaction mixture is worked up, water may be also be added to the concentrated filtrate of the hydrogenolysis reaction mixture, then filtered, to yield the mesylate trihydrate salt of the compound of formula (I) as the final product. If low-pyrogen or pyrogen-free conditions are employed, the isolated mesylate salt trihydrate is suitable for use in parenteral applications.

If the removal of the protecting group by hydrogenolysis is not performed in the presence of mesylate trihydrate, the reaction may be conducted in a less polar solvent, e.g., tetrahydrofuran, to achieve the free base compound. A separate reaction step to make the mesylate salt trihydrate may, of course, be conducted starting from the free base, if so desired.

The mesylate salt trihydrate, similar to the anhydrous mesylate and free base, possesses selective neuroprotective activity, based upon its antiischemic activity and ability to block, excitory amino acid receptors. The preferred procedure for evaluating the neuroprotective activity of this compound is that described by Ismail A. Shalaby, et al., *J. Pharm. Exper. Ther.*, 260, 925 (1992). This article is incorporated herein by reference in its entirety and described below.

Cell culture. Seventeen day fetal rat (CD, Charles River Breeding Laboratories, Inc., Wilmington, Mass.) hippocampal cells are cultured on PRIMARIA culture plates (Falcon Co., Lincoln Park, N.J.) for 2 to 3 weeks in serum containing culture medium (minimum essential medium with nonessential amino acids, containing 2 mM glutamine, 21 mM glucose, penicillin/streptomycin (5000 U each), 10% fetal bovine serum (days 1–7) and 10% horse serum (days 1–21). Cells are either plated on 96-well microtiter plates at a density of 80,000 cells per well or on 24-well culture plates at a density of 250,000 cells per well. Cultures are grown at 37° C. in a humidified $CO_2$ tissue culture incubator containing 5% $CO_2$/95% air. Proliferation of nonneuronal cells is controlled by adding 20 μM uridine and 20 μM 5-fluoro-2-deoxyuridine (Sigma Chemical Co., St. Louis, Mo.) from days 6 to 8 of culture. Culture media is exchanged every 2 to 3 days with fresh stock.

Glutamate toxicity. The cultures are assessed for glutamate toxicity 2 to 3 weeks from initial plating. Culture media is removed and cultures rinsed twice with a CSS (in millimolar.): NaCl, 12-; KCl, 5.4; $MgCl_2$, 0.8; $CaCl_2$, 1.8; glucose, 15; and 4-(2-hydroxyethyl)-1-piperazineethanesulfonic acid, 25 mM (pH 7.4). Cultures are then exposed for 15 minutes (37° C.) to various concentrations of glutamate. After this incubation, cultures are rinsed 3 times with glutamate-free CSS and twice with fresh culture medium without serum. The cultures are then incubated for 20 to 24 hours in serum-free culture medium. The compound being tested is added 2 minutes before and during the 15-minute exposure to glutamate. In some experiments, the compound is added at different times after the glutamate exposure and for the following 20 to 24 hours.

Cell viability is routinely assessed 20 to 24 hours after the excitotoxin exposure by measuring the activity of the cytosolic enzyme LDH. LDH activity is determined from the culture medium of each of the 96 wells of the microtiter plates. A 50-μl sample of the media is added to an equal volume of sodium-phosphate buffer (0.1 M, pH 7.4) containing 1.32 mM sodium pyruvate and 2.9 mM NADH. The 340 nm absorbance of the total reaction mixture for each of the 96 wells is monitored every 5 seconds for 2 minutes by an automated spectrophotometric microtiter plate reader (Molecular Devices; Menlo Park, Calif.). The rate of absorbance is automatically calculated using an IBM SOFTmax program (version 1.01; Molecular Devices) and is used as the index of LDH activity.

Morphological assessment of neuronal viability is determined using phrase contrast microscopy. The 96-well culture plates do not permit good phase-contrast imagery, so cells cultured on 24-well plates are used for this purpose. Quantitatively, both culture platings are equally sensitive to glutamate toxicity, and display 2- to 3-fold increases in LDH activity 24 hours after exposure to 0.1 to 1.0 mM glutamate.

Reagents. DTG can be purchased from Aldrich Chemical Company (Milwaukee, Wis.), and haloperidol from Research Biochemicals Inc. (Natick, Mass.). Spermine can be purchased from Sigma Chemical Co. (St. Louis, Mo.). Horse and fetal bovine serum can be purchased from Hyclone (Logan, Utah). Culture medium, glutamine and penicillin/streptomycin can be purchased from Gibco Co. (Grand Island, N.Y.).

Data analysis. Neurotoxicity can be quantified by measuring the activity of LDH present in the culture medium 20 to 24 hours after glutamate exposure. The increased LDH activity in the culture media correlates with destruction and degeneration of neurons (Koh and Choi, 1987). Because actual levels of LDH vary from different cultures, data are routinely expressed relative to buffer-treated sister wells of the same culture plate. To obtain an index of LDH activity from glutamate and drug-treated cultures, the LDH values from control cultures are subtracted from that of the treatment groups. Data for drug treatments is expressed as a percentage of the increase in LDH induced by 1 mM glutamate (or NMDA) for each experiment. Concentrations of NMDA antagonists required to reverse 50% of the LDH increase induced by excitotoxins ($IC_{50}$) are calculated using log-probit analysis from the pooled results of three independent experiments.

The selective neuroprotective antiischemic and excitatory amino acid blocking activities of the mesylate salt trihydrate of this invention render it useful in the treatment of disorders selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence.

In the systemic treatment of such disorders, the dosage is typically from about 0.02 to 250 mg per kg per day (0.001–12.5 g per day in a typical human weighing 50 kg) in single or divided doses, regardless of the route of administration. A more preferred dosage range is from about 0.15 mg per kg per day to about 250 mg per kg per day. Of course, depending upon the exact nature of the illness and the condition of the patient, doses outside this range may be prescribed by the attending physician. The oral route of administration is generally preferred. However, if the patient is unable to swallow, or oral absorption is otherwise impaired, the preferred route of administration will be parenteral (i.m., i.v.) or topical.

The mesylate salt trihydrate may be administered in the form of pharmaceutical compositions together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

The following Examples illustrate the processes of the present invention and the preparation of the compounds of the invention. Melting points are uncorrected. NMR data are reported in parts per million (δ) and are referenced to the deuterium lock signal from the sample solvent (deuterochloroform, unless otherwise specified). Commercial reagents were utilized without further purification.

EXAMPLE 1

(2S)-1-(4-Benzyloxyphenyl)-2-(4-hydroxy-4-phenylpiperidin-1-yl)-1-propanone Dibenzoyl-D-Tartate Salt Racemic 1-(4-benzyloxyphenyl)-2-(4-hydroxy-4-phenylpiperidin-1-yl)-1-propanone (100 g, 0.24 mol) and dibenzoyl D-tartaric acid (86.3 g, 0.24 mol) were added to acetone (1.5 L) under a nitrogen atmosphere to give a yellowish solution. After the solution was heated for 1 hour at 48 to 52° C., a thick white slurry was formed. The slurry was heated an additional 6.5 hours and then cooled to 20 to 25° C. The solid was granulated for 1 hour at 20 to 25° C., filtered, and then the cake washed with fresh acetone (0.2 L). The white solid was dried in vacuo for 12 to 15 hours at 35 to 40° C. to give 155.6 g of the title compound (84% yield). mp 140.1–141.1° C.; $[\alpha]_D^{25}$+65.4 (c 4.5, $CH_3OH$). Chiral HPLC showed that the salt contained 0.9% of the (−) enantiomer, (2R)-1-(4-benzyloxyphenyl)-2-(4-hydroxy-4-phenylpiperidin-1-yl)-1-propanone.

EXAMPLE 2

(2S)-1-(4-Benzyloxyphenyl)-2-(4-hydroxy-4-phenylpiperidin-1-yl)-1-propanone

Under a nitrogen atmosphere, (2S)-1-(4-benzyloxyphenyl)-2-(4-hydroxy-4-phenylpiperidin-1-yl)-1-propanone dibenzoyl D-tartate salt (150.0 g, 0.19 mol) was suspended in ethyl acetate (0.45 L, 3.0 mL/g of tartrate salt) and water (0.75 L, 50 mL/g of tartrate salt) containing $NaHCO_3$ (51.0 g, 0.61 mol). The mixture was stirred for 2 hours at 20 to 25° C. while $CO_2$ was liberated ($pH_f$=8.1). Stirring was stopped and the clear layers were allowed to separate. The lower aqueous layer was separated and then the ethyl acetate layer was concentrated to 0.1 L at 25 to 30° C. under reduced pressure. The concentrate was slowly added over 2 hours to hexanes (0.5 L) cooled to 15 to 20° C., The slurry was concentrated to 0.4 L, the solids were granulated for 1 hour at 15 to 20° C., filtered, and then washed with additional hexanes (80 mL). (2S)-1-(4-benzyloxyphenyl)-2-(4-hydroxy-4-phenylpiperidin-1-yl)-1-propanone was dried in vacuo for 12 hours at 40 to 45° C. to give 77.8 g of white free base in 96.7% yield. M.p. 102.5–103.8; $[\alpha]_D^{25}$+18.9 (c 8.9, $CH_3OH$). $^1H$ NMR ($CDCl_3$) δ 8.13 (d, J=8.7 Hz, 2H) 7.2–7.4 (m, 10H), 7.00 (d, J=8.7 Hz, 2H), 5.13 (s, 2H), 4.11 (g, J=6.8 Hz, 1H), 2.6–2.9 (m, 4H), 2.0–2.2 (m, 2H), 1.7–1.8 (m, 2H), 1.31 (d, J=6.8 Hz, 3H). $^{13}C$ NMR ($CDCl_3$) δ 199.69, 162.75, 136.47, 131.49, 129.72, 128.96, 128.55, 128.50, 127.77, 127.23, 124.80, 114.58, 71.44, 70.34, 64.78, 47.83, 44.62, 39.14, 38.79, and 12.28. Chiral HPLC showed that the (−) enantiomer, (2R)-1-(4-benzyloxyphenyl)-2-(4-hydroxy-4-phenylpiperidin-1-yl)-1-propanone was present at 1.2%.

EXAMPLE 3

(1S,2S)-1-(4-benzyloxyphenyl)-2-(4-hydroxy-4-phenylpiperidin-1-yl)-1-propanol

Over 20 minutes, (2S)-1-(4-benzyloxyphenyl)-2-(4-hydroxy-4-phenylpiperidin-1-yl)-1-propanone (75 g, 0.18 mol) was added to a suspension of lithium borohydride (3.15 g, 0.15 mol) in ethanol (0.75 L) maintained under a nitrogen atmosphere at 20 to 25° C. After stirring for about 5 minutes, a mild exotherm occurred raising the temperature to 27° C. The slurry was stirred for 42 hours at 20 to 25° C. when HPLC indicated that the reaction was complete. Water (37.5 mL) was added and the slurry was granulated for 1 hour at 20 to 25° C. The white solid was filtered and then washed with ethanol (75 mL), water (150 mL), and finally ethanol (75 mL). The product was dried in vacuo at 40 to 45° C. for 20 hours to give 65.3 g of the title compound. The (1S,2S) amino alcohol product was obtained in 78.3% yield and contained only 2.3% of diastereomers. M.p. 158–161° C., $[\alpha]_D^{25}$+38.7 (c 6.1, $CH_3OH$)

EXAMPLE 4

(1S,2S)-1-(4-Hydroxyphenyl)-2-(4-hydroxy-4-phenylpiperidino)-1-propanol, Methanesulfonate Salt Trihydrate Five percent palladium on carbon catalyst (0.75 g, 50% water-wet), (1S,2S)-1-(4-benzyloxyphenyl)-2-(4-hydroxy-4-phenylpiperidin-1-yl)-1-propanol (5.0 g, 12.0 mmol), ethanol (62.5 mL), and methanesulfonic acid (1.15 g, 12.0 mmol) were combined in a Parr pressure reactor under a nitrogen atmosphere. The nitrogen atmosphere was exchanged for hydrogen (3×25 psi) and then the hydrogen pressure was increased to 50 to 55 psi. The mixture was heated and stirred at 50 to 55° C. for 5 hours when HPLC indicated that the reaction was complete. The hydrogen gas was slowly vented, the reactor flushed with nitrogen, and then the warm (50° C.) reaction mixture was filtered through Celite. The Celite filter cake was washed with ethanol (5 mL). The combined wash and filtrate were concentrated in vacuo to 10 mL. Water (17.5 mL) was added and the solution was concentrated at atmospheric pressure until a distillate temperature of 76° C. was obtained. The clear solution was slowly cooled over 1 hour to 15 to 20° C. and then cooled further to 0 to 5° C. After granulating for 1 hour at 0 to 5° C., the thick slurry was filtered and the cake washed with cold water (5° C., 2.5 mL). The solid was dried for 18 hours at 20 to 25° C. to give 4.71 g of the title compound for an 83% yield. The product was identical to an authentic sample of the title compound. If low-pyrogen water and pyrogen-free conditions are employed in the above procedure, isolated title compound is suitable for parenteral applications.

What is claimed is:

1. A (2S)-compound of formula (II)

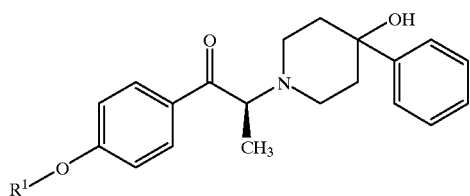

(II)

or a salt thereof, wherein $R^1$ is hydrogen or a protecting group selected from the group consisting of benzyl, $(C_1-C_6)$ alkylbenzyl, $(C_1-C_6)$alkoxylbenzyl, tri$(C_1-C_6)$alkylsilyl, acyl and aroyl, and the salt is the diaroyl D-tartrate,— wherein the diaroyl D-tartrate is dibenzoyl D-tartrate or di-p-toluoyl D-tartrate.

2. A compound according to claim 1 wherein $R^1$ is benzyl and is in the form of the dibenzoyl D-tartrate salt.

3. A process for the preparation of the methanesulfonate trihydrate salt of (1S,2S)-1-(4-hydroxyphenyl)-2-(4-hydroxy-4-phenylpiperidin-1-yl)-1-propanol:

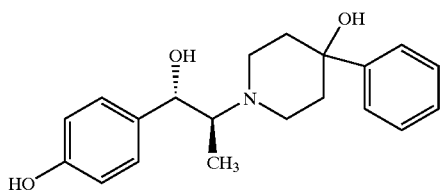

(I)

comprising the steps of (i) placing a compound of formula (IV):

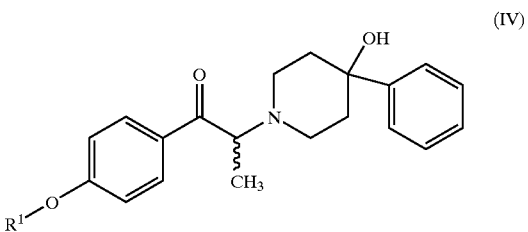

(IV)

together with a diaroyl tartrate compound selected from the group consisting of dibenzoyl D-tartrate and di-p-toluoyl D-tartrate;

(ii) treating the D-tartrate salt product of step (i) with a weak base to obtain a compound of formula (II):

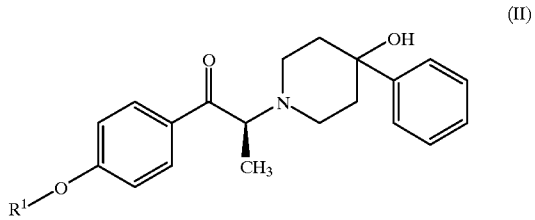

(II)

(iii) reducing the carbonyl group of a compound of formula (II) via reaction with an alkali metal borohydride; and (iv) cleaving off the protecting group $R^1$ of a compound of formula (III):

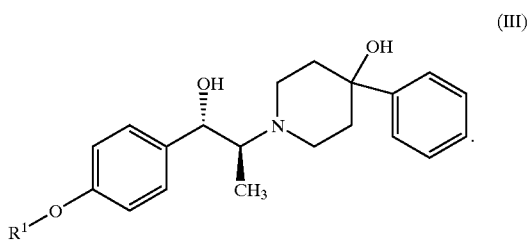

(III)

in the presence of methanesulfonic acid.

* * * * *